United States Patent
Mizuno

(10) Patent No.: US 6,833,273 B2
(45) Date of Patent: Dec. 21, 2004

(54) METHOD FOR EVALUATING CONCENTRATION OF METALLIC IMPURITIES IN SILICON WAFER

(75) Inventor: Michihiro Mizuno, Fukushima (JP)

(73) Assignee: Shin-Etsu Handotai Co., Ltd., Tokyo (JP)

( * ) Notice: Subject to any disclaimer, the term of this patent is extended or adjusted under 35 U.S.C. 154(b) by 378 days.

(21) Appl. No.: 09/937,538

(22) PCT Filed: Jan. 18, 2001

(86) PCT No.: PCT/JP01/00301

§ 371 (c)(1),
(2), (4) Date: Sep. 25, 2001

(87) PCT Pub. No.: WO01/55716

PCT Pub. Date: Aug. 2, 2001

(65) Prior Publication Data

US 2003/0073240 A1 Apr. 17, 2003

(30) Foreign Application Priority Data

Jan. 26, 2000 (JP) ........................... 2000-016517

(51) Int. Cl.$^7$ ............................................ G01N 31/00
(52) U.S. Cl. ................. 436/40; 436/5; 436/73; 436/80; 436/178
(58) Field of Search .............. 73/715; 216/109; 252/79.3; 436/40, 5, 73, 80

(56) References Cited

U.S. PATENT DOCUMENTS 6,444,010 B1 * 9/2002 Watanabe ................ 75/715

FOREIGN PATENT DOCUMENTS

| EP | 0763735 | * 3/1997 |
| JP | 02-272359 | 11/1990 |
| JP | 409015174 | * 1/1997 |
| JP | 2000-002632 | 1/2000 |

* cited by examiner

Primary Examiner—Jill Warden
Assistant Examiner—Sam P. Siefke
(74) Attorney, Agent, or Firm—Hogan & Hartson, LLP

(57) ABSTRACT

A method for evaluating concentration of metal impurities contained in a silicon wafer, which comprises dropping concentrated sulfuric acid onto a surface of the silicon wafer to extract metal impurities solid-solubilized in the inside of the silicon wafer into the concentrated sulfuric acid, and chemically analyzing metal impurities contained in the concentrated sulfuric acid. The problem imposed on high sensitivity evaluation of metals contained in silicon bulk is, in addition to increase of sensitivity of analysis apparatus itself, how to extract metals contained in a silicon wafer to a surface and recover them. This problem can be solved by the method of the present invention.

15 Claims, 2 Drawing Sheets

METHOD FOR EVALUATING CONCENTRATION OF METALLIC IMPURITIES IN SILICON WAFER

TECHNICAL FIELD

The present invention relates to a method for quantitatively analyzing metals solid-solubilized in a silicon wafer.

BACKGROUND ART

It is known that, with recent use of finer semiconductor devices and higher integration degree thereof, metals contained in silicon wafers degrade device characteristics and markedly influence on yield of device production. In particular, it is known from many examples that Cu solid-solubilized in silicon wafers (also referred to as "bulk Cu" hereinafter) may be a cause of bad influences on the device characteristics. Therefore, a large number of gettering methods, cleaning methods and so forth have been researched for eliminating such metal impurities.

On the other hand, there is desired a method for analyzing such metal impurities, especially bulk Cu concentration, with high precision and high sensitivity for controlling the metal contamination during the wafer production processes such as polishing step and cleaning step.

As such a method for analyzing metals contained in silicon wafers, there are evaluation methods called one-drop method, step etching method and so forth. These are dissolution methods in which all or a part of a silicon wafer is dissolved with a mixture of hydrofluoric acid and nitric acid (also referred to as "mixed acid" hereinafter) or the like in a gaseous phase or liquid phase and metals in the solution are quantified by an analysis apparatus.

There is also a method called an annealing combined method or the like. In this method, metals present in a silicon wafer is transferred to a wafer surface (or captured thereby) by subjecting the wafer to a heat treatment, then an oxide film on the wafer surface is decomposed in a vapor phase, recovery solution is run over the entire surface of the wafer, and the recovery solution is subjected to quantitative analysis using an analysis apparatus.

Analysis apparatuses generally used for the analysis of dissolution solution or recovery solution obtained by these methods include frameless atomic absorption spectrophotometer (abbreviated as "AAS" hereinafter), inductively coupled plasma mass spectrometer (abbreviated as "ICP-MS" hereafter) and so forth.

Further, although it is not a method of directly evaluating metals contained in silicon wafers, there are also contemplated a method of directly analyzing metals contained in chemical solutions used in cleaning step and so forth, and other methods.

The conventional dissolution methods require enormous labor for maintenance and management of analysis apparatus and prevention of contamination from environment, and are likely to suffer from significant fluctuation of human factors. For example, when Cu is contained in a silicon wafer in an amount of about $1 \times 10^{13}$ atoms/cm$^3$ and the analysis is performed by the dissolution methods, detection cannot be achieved unless the analysis apparatus used for analyzing a final dissolution solution has an ability to detect about 0.1 ppt of the metal.

Further, for example, analysis may become possible at a level exceeding the ability of the analysis apparatus by concentrating the dissolution solution and so forth. In such a case, however, contamination which is newly introduced from a platinum crucible used for the concentration or external environment, i.e., interfusion of metals, is expected, and therefore good measurement precision could not necessarily be obtained.

In recent years, the sensitivity of analysis apparatuses, such as frameless atomic absorption spectrophotometer (AAS) and inductively coupled plasma mass spectrometer (ICP-MS), has shifted to sensitivity of ppt level. As for the ability of generally used apparatuses such as frameless atomic absorption spectrophotometer and inductively coupled plasma mass spectrometer, for example, the frameless atomic absorption spectrophotometer is at about 100 ppt level, and even the inductively coupled plasma mass spectrometer is at about 1 ppt level for Cu.

However, for evaluation of metals in silicon bulk, it is a problem how to extract metals contained in inside of silicon to the surface and collect them, in addition to the increase of sensitivity of the analysis apparatus itself.

When Cu is analyzed by the dissolution methods such as the one-drop method and the step etching method by using currently used apparatuses, the analysis could not actually be performed unless $1 \times 10^{14}$ to $1 \times 10^{16}$ atoms/cm$^3$ or more of Cu is contained in a silicon wafer, because the apparatuses show bad recovery yield from inside of the silicon.

Furthermore, in the annealing combined method, although metals comes to be likely to gather at the surface by the heat treatment, the recovery yield, i.e., the ratio (gettering efficiency) of metals transferred to the wafer surface (captured at the wafer surface) is as low as 0.1% or less for Cu in low resistivity silicon wafers which are doped with boron at a high concentration and so forth. Therefore, metals contained in the inside of silicon scarcely gather at the surface, and also there is resistivity dependency, so that measurement has a large error. In addition, it is expected that contamination and so forth are newly invited by the heat treatment at a high temperature (about 650° C.). Even by this method, the analysis could not actually be performed unless $1 \times 10^{13}$ to $1 \times 10^{14}$ atoms/cm$^3$ or more is contained in a silicon wafer.

Further, the method of directly analyzing metals contained in a chemical solution used in cleaning step etc., for example, suffers from problems that detection requires concentration of the solution by heating or the like because only a small amount of metal impurities are contained in a large volume of the chemical solution, the chemical solution may be an inhibition factor for the analysis depending on its nature, and strikingly decrease sensitivity of the analysis for metals when a large volume of the chemical solution is present. For example, these are caused in a case where Cu should be analyzed in a cleaning solution containing a large volume of sulfuric acid. For the analysis of Cu contained in such a solution, a special method such as an evaluation method utilizing a radioisotope must be used, and thus the method must be in a large scale in view of evaluation time and apparatus. Further, this is just an evaluation of metals in the chemical solution, and it is not for accurately determining concentration of metal impurities in a silicon wafer, which is the original matter of interest.

DISCLOSURE OF THE INVENTION

Accordingly, an object of the present invention is to provide a pretreatment method for analyzing a concentration of a metal, in particular, Cu, contained in a silicon wafer with high sensitivity in a simple manner.

In order to achieve the aforementioned object, the present invention provides a method for evaluating concentration of metal impurities contained in a silicon wafer, which comprises dropping concentrated sulfuric acid onto a surface of the silicon wafer to extract metal impurities solid-solubilized in the inside of silicon wafer into the concentrated sulfuric acid, and chemically analyzing metal impurities contained in the concentrated sulfuric acid.

If the metals in the bulk are recovered by using concentrated sulfuric acid as described above, the metals once recovered in the concentrated sulfuric acid scarcely diffuse again into the inside of the bulk, and thus the metals can be efficiently extracted to the wafer surface. Further, the wafer surface is unlikely to be roughened, and therefore favorable evaluation of wafer can be performed. Moreover, since the evaluation can be performed by using a few drops of concentrated sulfuric acid, the influences of sulfuric acid such as decrease of analytical sensitivity can be minimized.

Specifically, the method for extracting metal impurities solid-solubilized in the inside of a silicon wafer into concentrated sulfuric acid is performed by dropping an arbitrary amount of concentrated sulfuric acid onto the aforementioned silicon wafer surface, putting another uncontaminated wafer on the concentrated sulfuric acid on the aforementioned silicon wafer to hold the concentrated sulfuric acid between the wafers, and subjecting the whole of the wafers in that state to a heat treatment.

The uncontaminated wafer is put on the dropped concentrated sulfuric acid in order to facilitate the sulfuric acid to uniformly spread over the entire surface of the wafer. Further, it is also used in order to prevent the concentrated sulfuric acid from rapidly evaporating or scattering during the heat treatment to secure safety.

Therefore, the material of the uncontaminated wafer used for preventing scattering of concentrated sulfuric acid and so forth (also referred to as a "protective wafer") is not particularly limited, and it is also possible to use quartz glass or the like. However, if spread of the concentrated sulfuric acid is taken into consideration, use of a silicon wafer, in particular, such a wafer having a surface subjected to etching treatment (also referred to as "CW wafer") provides favorable uniform spread of concentrated sulfuric acid over the entire surface of wafer, and easy delamination after the treatment. Moreover, if the CW wafer is subjected to a treatment with concentrated sulfuric acid beforehand, metal impurities in the CW wafer can be eliminated. By using such a CW wafer, contamination of a wafer to be evaluated from the CW wafer (or contamination of the concentrated sulfuric acid from the CW wafer) can be suppressed as much as possible, and thus the precision of the evaluation can be increased. Further, a wafer of n-type is originally unlikely to be contaminated, and therefore particularly suitable for the protective wafer.

The aforementioned heat treatment is preferably performed at a temperature in the range of 100° C. to 290° C.

This is because diffusion of metal impurities is promoted so that transfer of the impurities from inside of the wafer to the wafer surface should be facilitated.

As for the method of chemically analyzing metal impurities contained in the concentrated sulfuric acid, after metal impurities solid-solubilized in the inside of silicon wafer are extracted into the concentrated sulfuric acid, the concentrated sulfuric acid on the silicon wafer is neutralized by exposing it to an ammonia gas atmosphere, and then a recovery solution for recovering metals remaining on the silicon wafer is dropped onto the wafer surface, run over the wafer surface, then recovered and chemically analyzed.

This procedure enables efficient recovery of metals gathered on the wafer surface.

The aforementioned recovery solution consists of hydrofluoric acid/aqueous hydrogen peroxide, hydrochloric acid/aqueous hydrogen peroxide, hydrofluoric acid/nitric acid or aqua regia. Since these recovery solutions are coexistent with an oxidizing agent, they enable easy recovery of metal impurities.

Further, the aforementioned chemical analysis may be frameless atomic absorption spectrometry or inductively coupled plasma mass spectrometry.

This is because apparatuses used for these analyses are generally used apparatuses and they can analyze chemicals used for the present invention and so forth. However, the chemical analysis method is not limited to these, and the apparatus may be an apparatus that can analyze a solution recovered according to the present invention with further higher sensitivity.

Among evaluations of metals contained in silicon wafers, the analysis method of the present invention is particularly preferred for analysis of Cu. While metal impurities such as Cu, Ni, Ag and the like are basically recovered in concentrated sulfuric acid, Cu, in particular, is likely to remain in the bulk, and it is the current major problem that it cannot be recovered efficiently. The present invention concerns evaluation in which such Cu can be recovered at high yield.

Moreover, the method of the present invention is particularly suitable for evaluation of a silicon wafer having a resistivity of 1 $\Omega$·cm or less.

A wafer showing low resistivity of 1 $\Omega$·cm or less is significantly influenced by the resistivity in the conventional annealing combined method and so forth, and Cu and so forth can scarcely be recovered when the resistivity is low (amount of dopant is large). That is, it has been particularly difficult so far to evaluate metal contamination in the bulk of low resistivity wafer.

However, the method of the present invention suffers from little influence of resistivity, and it enables evaluation for a wide range of resistivity covering from a high resistivity wafer of 10 $\Omega$·cm or higher to a low resistivity wafer of about 0.001 $\Omega$·cm.

As clearly understood from the above explanation, the recovery yield of metals from inside of wafer is increased by the treatment with concentrated sulfuric acid according to the present invention. Further, it enables quantitative evaluation of a low resistivity wafer, which cannot have been evaluated thus far. Even by using a currently used apparatus for frameless atomic absorption spectrometry (lower detection limit is about 100 ppt), the analysis is possible and the sensitivity is improved, if about $1\times10^{11}$ atoms/cm$^3$ of impurities are contained in a silicon wafer.

Further, according to the present invention, fluctuation of precision due to exogenous factors is also suppressed, and the method enables detection even at a low Cu concentration, if the Cu is contained at a concentration of $1\times10^{9-11}$ atoms/cm$^3$ or more, and sensitivity and measurement precision are also improved.

BEST MODE FOR CARRYING OUT THE INVENTION

Hereafter, embodiments of the present invention will be explained. However, the present invention is not limited to these.

Figure 1:
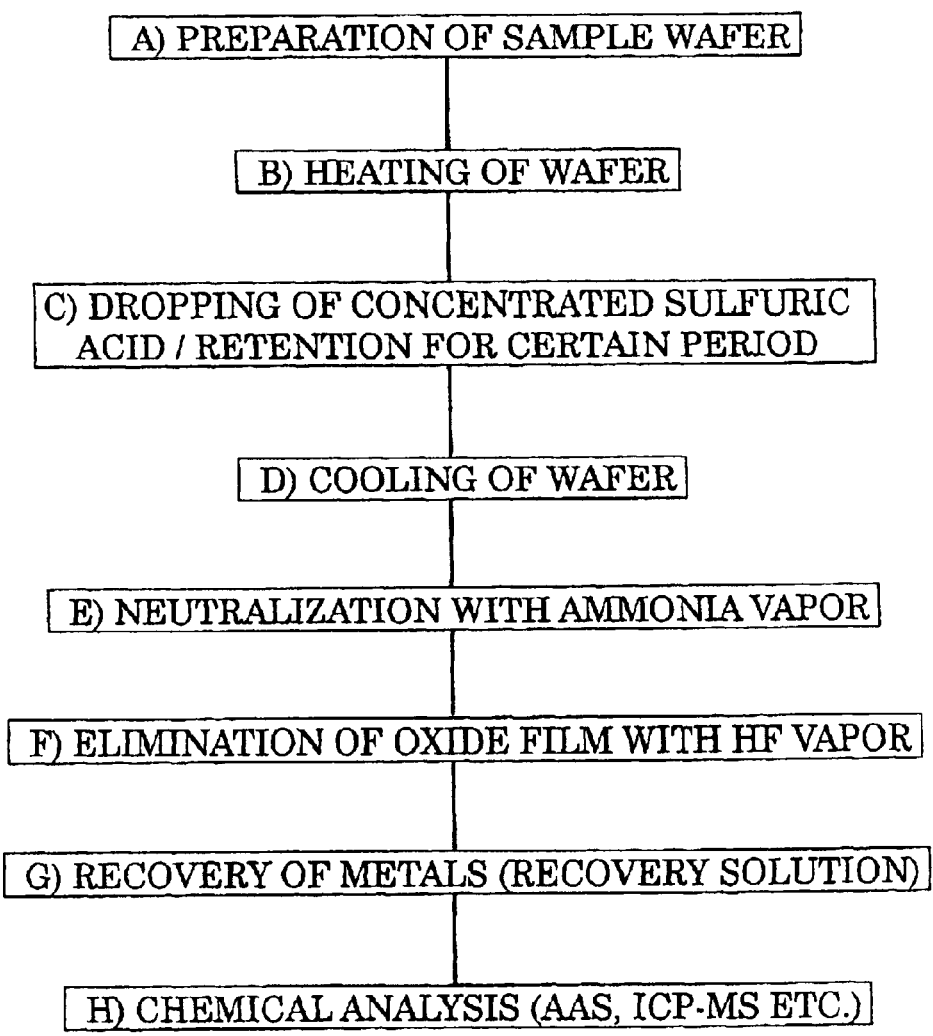
FIG. 1 is a schematic flow diagram representing the evaluation procedure according to the present invention.
Figure 2:
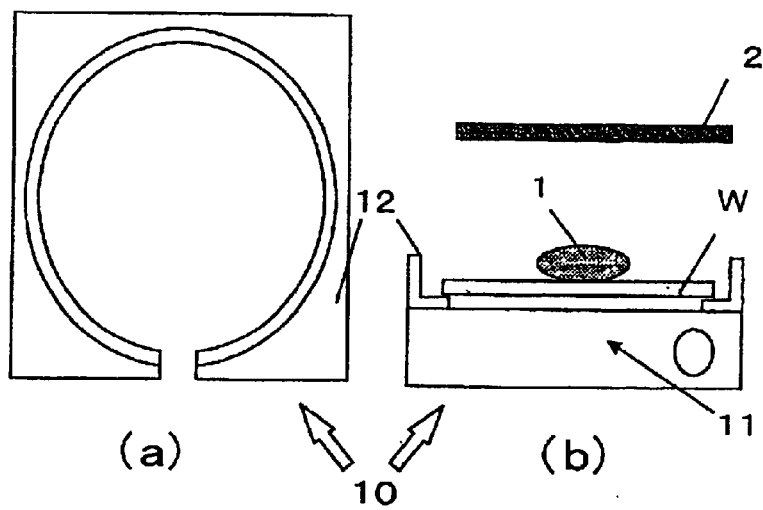
FIG. 2 is a schematic view of an exemplary heat treatment apparatus used for the present invention. In the figure, (a) is a plan view and (b) is a side view.

The present invention will be explained in detail with reference to the drawings. FIG. 1 is a schematic flow diagram representing the evaluation procedure according to the present invention, and FIG. 2 is a schematic view of an exemplary heat treatment apparatus used for the present invention.

The procedure is as shown in the schematic flow diagram of FIG. 1.

A) First, a sample wafer W to be evaluated is prepared. Although this wafer is not particularly limited, its surface is preferably mirror-polished.

Then, there is prepared a heat treatment apparatus 10 comprising a hot plate 11, on which a special quartz jig 12 is disposed. Care must be taken so that there should not be contamination due to this heat treatment apparatus.

While the configuration of this heat treatment apparatus is not particularly limited, an apparatus shown in FIG. 2 has been used as an example. In order to prevent contamination from the outside as much as one can, this heat treatment apparatus 10 has a structure that a quartz plate 12 or an uncontaminated silicon wafer is placed on a heater such as the hot plate 11, and an air gap was provided so that the sample wafer should not be in direct contact with the hot plate or the like.

B) The sample wafer W is placed in this heat a treatment apparatus 10 so that the mirror surface (PW surface) should be the upper surface, and the temperature of the hot plate 11 is controlled so that the temperature of the surface of the sample wafer W should become an arbitrary predetermined temperature (for example, 200° C.).

This temperature is preferably controlled to be within the range of about 100–290° C. The temperature is controlled to be 100° C. or higher in order to promote the diffusion of metals, and it is controlled to be 290° C. or lower because the decomposition temperature of sulfuric acid is about 290° C. and the boiling point thereof is 317° C.

Further, this heat treatment is preferably performed under such a condition that a uniform concentrated sulfuric acid film should adhere to the entire surface of the sample wafer. At a high temperature, sulfuric acid becomes mist and evaporates from the gap between the wafers. Therefore, the concentrated sulfuric acid film is more likely to become uneven by heating at a higher temperature. Although the recovery is possible even in such a state, it is preferred that a uniform sulfuric acid film should adhere to the entire surface of wafer. When the temperature exceeds about 220° C., evaporation of sulfuric acid mist (white smoke) comes to be observed. Therefore, the heat treatment is preferably performed at a temperature lower than that level, but higher as much as possible. The heat treatment is particularly preferably performed in the range of 180–220° C.

C) Then, a few drops of concentrated sulfuric acid 1 of high purity are dropped onto the PW surface of the sample wafer W approximately at the center of the wafer. Thereafter, an uncontaminated CW wafer 2 (protective wafer) having the same diameter is placed thereon to bond the sample wafer W and the CW wafer 2 to hold the concentrated sulfuric acid between them. In this state, the wafers are heated for an arbitrary period of time. In this operation, since the concentrated sulfuric LP, acid 1 begins to evaporate as white smoke immediately after it was dropped, the CW wafer 2 should be quickly placed.

Although the wafer 2 bonded in this operation is not limited to a silicon wafer, it is preferably a silicon wafer, in particular, such a wafer of n-type subjected to an etching treatment, if contamination and so forth are taken into consideration. This is because a wafer of n-type suffers from less metal contamination compared with a p-type wafer. Further, the use of a wafer having a surface subjected to an etching treatment (CW wafer) described above favorably results in uniform spread of the concentrated sulfuric acid over the entire surface of the wafer, and also provides easy separation after the treatment.

If the heat treatment is performed under such a sandwiching state as described above, the concentrated sulfuric acid 1 spreads over the entire surface of wafer through a gap formed by the sample wafer W and the CW wafer 2 due to the weight of CW wafer 2 and decrease of viscosity of the concentrated sulfuric acid 1 caused by heating, and thus a uniform sulfuric acid film will be formed.

In the method described above, the sample wafer W is heated and then the concentrated sulfuric acid 1 is dropped. However, the concentrated sulfuric acid 1 may be dropped onto the sample wafer W, then the CW wafer 2 may be placed to obtain the sandwiching state, and thereafter they may be placed in the heat treatment apparatus 10 and heated.

D) After completion of the heating, the bonded sample wafer W and CW wafer 2 are taken out from the hot plate 11, and cooled at a room temperature. After the cooling, two of the wafers are carefully separated. At this time, it is confirmed if the concentrated sulfuric acid 1 has spread over the entire surface of the wafer.

Depending on this spreading state, the dropped amount of the concentrated sulfuric acid 1 or the heating temperature is controlled. If the amount of the concentrated sulfuric acid 1 is too small, it is not spread over the entire surface. If it is too large, it may be spilled during the heating or the analysis sensitivity may be decreased by sulfuric acid, and thus it is not preferred for quantitative analysis. When the evaluation was performed by dropping concentrated sulfuric acid onto a mirror surface of a 6-inch wafer, it was found that the evaluation can be preferably performed with two drops (about 30 mg) of concentrated sulfuric acid 1 at a heat treatment temperature of about 200° C.

In addition, care must be sufficiently taken for contamination from the outside. For example, during the delamination, attention must be paid not to touch the surface on which concentrated sulfuric acid 1 has adhered with fingers.

After the delamination, the concentrated sulfuric acid 1 has adhered to both of the sample wafer W and the CW wafer 2. The ratio of adhered concentrated sulfuric acid was confirmed. As a result, it was found that the concentrated sulfuric acid adhered at a ratio of about 1:1. Therefore, it is sufficient to evaluate the concentrated sulfuric acid adhered on either one of the wafers. In the analysis described later, only the sample wafer W was evaluated. However, if the concentrated sulfuric acid on the surface of the CW wafer 2 is also evaluated, the sample quantity n is increased, and thus the measurement is performed with higher precision while preventing fluctuation and so forth.

E) Then, the surface of the sample wafer W on which the concentrated sulfuric acid 1 has adhered is neutralized with ammonia vapor. If the concentrated sulfuric acid used for extracting the metal can be recovered as it is and analyzed, it would be preferred. However, it was difficult to recover the solution spreading on the wafer surface. Therefore, after the metal was extracted into concentrated sulfuric acid, it was neutralized to adhere the metal on the wafer surface and the metal was treated by using another solution, which allowed simpler recovery. This neutralization treatment can be performed by placing the sample wafer W over a container containing aqueous ammonia so that the surface of the sample wafer W on which the concentrated sulfuric acid 1 has adhered should face to the aqueous ammonia to expose it to ammonia. The concentrated sulfuric acid 1 on the wafer reacts with ammonia vapor to form ammonium sulfate, and thus it is neutralized. This neutralization is employed for realizing stable recovery of metals.

F) After completion of the neutralization operation, an oxide film and so forth present on the wafer surface is decomposed in a vapor phase by using HF vapor. This is because, when the recovery solution is run over the wafer, it cannot be run well, if an oxide film or the like is formed on the wafer surface, and thus it becomes difficult to recover the metal adhering to the surface. Therefore, the oxide film is decomposed to make the surface hydrophobic. This treatment is not need to be performed for a wafer on which an oxide film is not particularly formed.

G) Then, impurities existing on the wafer surface are recovered. A recovery solution is run over the wafer surface, and recovered. As the recovery solution, hydrofluoric acid/aqueous hydrogen peroxide, hydrochloric acid/aqueous hydrogen peroxide, hydrofluoric acid/nitric acid, aqua regia and so forth may be used. If 1% HF+15% $H_2O_2$ is used as the recovery solution, metal adhering to the surface, especially Cu, can be recovered at a ratio of about 80–90%.

However, since a large amount of ammonium sulfate has adhered on the wafer surface in the present invention, such a high recovery yield as mentioned above cannot be obtained even if a solution of hydrofluoric acid/aqueous hydrogen peroxide is used. When ammonium sulfate exists, the recovery yield on the wafer surface is reduced to about 45% in contrast to a case where ammonium sulfate does not exist.

However, even if the recovery yield at the wafer surface is reduced, the total recovery yield from the inside of silicon bulk is increased compared with conventional evaluation methods and hence measurement precision is improved, because the recovery yield by the concentrated sulfuric acid 1 is improved (there is attained a recovery yield of about 75%). Further, because of very small amount of sulfuric acid to be used, i.e., a few drops, the decrease of sensitivity due to sulfuric acid is suppressed as much as possible. However, it is more preferable to use a recovery solution that is not influenced by ammonium sulfate, but improves the recovery yield in this step.

H) Metal concentration in this recovery solution that has used for the recovery of metals adhering to the wafer surface is analyzed by AAS or ICP-MS.

Although about 75% of the bulk Cu is extracted in the thin film of concentrated sulfuric acid 1, for example, according to this procedure as described above, only about 45% of the extracted metal can be recovered into a recovery solution due to the presence of ammonium sulfate. That is, the substantial recovery yield of the bulk Cu is about 34%. A recovery solution in this state is subjected to the quantitative analysis by AAS or ICP-MS.

Figure 3:
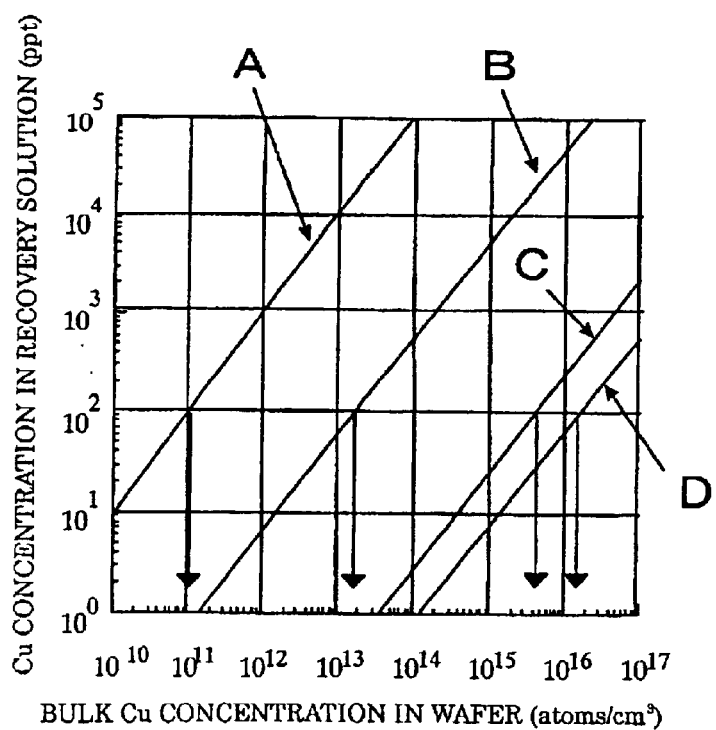
FIG. 3 shows relationship between Cu concentration in recovered solution and Cu concentration contained in inside of wafer. In the figure, A represents the relationship in the method of the present invention, B represents the same in the annealing combined method, C represents the same in the one-drop method, and D represents the same in the step etching method.

As a result of conversion considering such a recovery yield, the relationship of the Cu concentration actually contained in the bulk with the Cu concentration in the recovery solution to be subjected to the quantitative analysis is represented as shown in FIG. 3.

That is, the relationship of A shown in FIG. 3 is obtained according to the present invention, and it means that, for example, if 1000 ppt of Cu is detected by AAS etc., the concentration in the sample wafer is about $1 \times 10^{12}$ atoms/$cm^3$.

Similar relationships obtained by performing the measurement using the conventional methods are shown in FIG. 3.

This correlation diagram is obtained by using a sample having a resistivity of about 0.008 Ω·cm. The evaluation results were obtained by analyses of a solution recovered by using an HF recovery solution after a heat treatment at 650° C. in the annealing combined method (B in FIG. 3), a solution obtained after etching of 0.15 μm of wafer surface with 1.125 ml of mixed acid in the one-drop method (C in FIG. 3), and a solution obtained after etching of 1 μm of wafer surface with 25 ml of mixed acid in the step etching method (D in FIG. 3).

That is, as for a case where the pretreatment according to the present invention is performed and then the evaluation is performed by using AAS, since the effective lower detection limit of the apparatus itself is about 100 ppt, it is calculated from the recovery yield shown in FIG. 3 that the detection is possible if about $1 \times 10^{11}$ atoms/$cm^3$ of Cu is contained in the wafer. The lower detection limit of this evaluation method is about $1 \times 10^{11}$ atoms/$cm^3$ when AAS is used, or about $1 \times 10^9$ atoms/$cm^3$ when ICP-MS is used. However, this lower detection limit is influenced by the sensitivity of the apparatus itself, such as AAS and ICP-MS, and the lower detection limit can further be lowered if an analysis apparatus of still higher sensitivity is available.

In a similar manner, when the lower detection limits of the conventional methods were verified, they are about $1 \times 10^{13}$ atoms/$cm^3$ for the annealing combined method, and about $1 \times 10^{16}$ atoms/$cm^3$ for the one-drop method and the step etching method, which are insufficient for evaluating Cu in the bulk. Thus, it can be understood that the sensitivity is improved in the evaluation method of the present invention.

In addition, it is said that detection sensitivity of AAS or ICP-MS is also decreased by the presence of sulfate ions. As for AAS, this is because sulfur shows absorption spectrum similar to that of Cu. As for ICP-MS, that is because molecular ions such as $^{32}S^{16}O^{16}O$ and $^{32}S^{32}S$ may reduce the spectral intensity of $^{63}Cu$. However, as a result of experiments, substantial influence was not observed in both of the apparatuses, if the sulfuric acid concentration in a sample for analysis (recovery solution) is 1 volume % or less. For example, if the evaluation is performed by using a few drops of sulfuric acid (about 30 mg) as in the present invention, a sulfuric concentration of 1 volume % or less can be obtained by diluting the final recovery solution about 7.4 times. Therefore, it is preferable to perform 10-fold dilution and use the diluted solution in an analysis apparatus such as AAS or ICP-MS for ease and convenience of the operation and so forth.

If the dilution is at such a level, the analysis can be performed with good precision without significantly reducing the sensitivity.

As described above, important points for high precision measurement of metals in the bulk, in particular, Cu, with increased sensitivity and precision are how to efficiently extract metal impurities solid-solubilized in a silicon wafer in a small amount, how to recover the metal with smaller loss during the operation, how to decrease substances that interfere with the analysis, and how much degree of sensitivity is secured in an analysis apparatus to be used, and thus a treatment using a few drops of sulfuric acid as in the present invention is preferred.

Moreover, in the evaluation method of the present invention, the evaluation could be achieved at a similar analytical sensitivity level, irrespective of specification of wafers, for example, conductivity type such as p-type and n-type, and the production methods such as the Czochralski method (CZ method) and the floating zone method (the FZ method).

Examples of the present invention will be explained hereafter.

EXAMPLE 1

In order to clarify the recovery yield of bulk Cu obtainable according to the present invention, experiments were performed by using intentional contamination. Evaluated were ten of low resistivity wafers (diameter: 150 mm, p-type, 0.008 Ω·cm, thickness: 625 μm, produced by the CZ method), of which evaluation was difficult by the conventional techniques.

The intentional contamination was handled by applying a solution containing Cu on the aforementioned wafers, and heating the wafers so that Cu should be uniformly diffused in the bulk portions. The degree of the intentional contamination was $3.2 \times 10^{14}$ atoms/cm$^2$.

Evaluation procedure and evaluation conditions according to the present invention were as follows.

(1) A special quartz jig and a sample wafer were placed on a hot plate, so that a mirror surface (PW surface) of the wafer should be an upper surface.
(2) Temperature of the hot plate was controlled so that the temperature at the wafer surface should become 200° C.
(3) Two drops (about 30 mg) of concentrated sulfuric acid of high purity (for example, TAMAPURE (trade name) Grade AA-100, concentration: 98%, produced by Tama Chemicals Co., Ltd.) was dropped onto the PW surface approximately at the center of the wafer.
(4) Then, an uncontaminated CW wafer having the same diameter was placed thereon, and the wafers were heated for 2 hours.
(5) After completion of the heating, the wafers were taken out from the hot plate by using a ceramic tweezers, and cooled to room temperature.
(6) After the cooling, the two wafers were carefully separated. At this time, it was confirmed if the concentrated sulfuric acid had spread over the entire surface of the wafer.
(7) The back surface of the sample wafer was held by vacuum tweezers, and the surface to which the concentrated sulfuric acid had adhered was brought close to separately prepared aqueous ammonia (for example, TAMAPURE (trade name) Grade AA-100, concentration: 20%, produced by Tama Chemicals Co., Ltd.), so that the sulfuric acid was neutralized with ammonia vapor. Within several minutes (about 5 minutes), the sulfuric acid film on the surface changed into white powder.
(8) After completion of the neutralization operation, the wafer was left in a container in which 50% HF solution was placed, so that the native oxide film on the wafer surface was decomposed in a vapor phase with HF vapor.
(9) Then, impurities existing on the wafer surface were recovered. As a recovery solution, 200 μl of 1% HF+15% $H_2O_2$ solution was used. This solution was run over the entire wafer surface, and collected.
(10) The recovery solution was diluted 10 times in order to prevent reduction of analytical sensitivity for Cu due to sulfate ions etc., and the Cu concentration in the solution was determined by using AAS. As AAS, SIMAA-6000 produced by Perkin-Elmer was used.

As a result of the measurement according to the present invention, the Cu concentration in the silicon wafer was estimated to be about $2 \times 10^{14}$ atoms/cm$^2$ to $3 \times 10^{14}$ atoms/cm$^2$. That is, the recovery yield, which is considered as concentration of metal recovered in concentrated sulfuric acid/initial contamination concentration, was about 60 to 90%, and it was about 75% on average.

According to the present invention, a high recovery yield was obtained as described above. In addition, under the evaluation conditions of this example, there were observed little fluctuation and good reproducibility of the measured value, as well as little fluctuation thereof due to human factors.

COMPARATIVE EXAMPLE 1

Then, the evaluation was performed by the annealing combined method, which was a conventional technique. Wafers used had the same specification as those used in Example 1, and intentionally contaminated wafer were used. The intentional contamination was performed also in the same manner as in Example 1. The degree of Cu contamination was a about $3.2 \times 10^{14}$ atoms/cm$^2$.

The annealing combined method was performed with the following evaluation procedure and evaluation conditions.

(1) A wafer was subjected to an annealing heat treatment at 650° C. for 2 hours in the presence of nitrogen gas.
(2) After the heat treatment, the wafer was cooled, and then left in a container in which 50% HF solution was placed, so that the native oxide film on the wafer surface was decomposed in a vapor phase with HF vapor.
(3) Then, 200 μl of 1% HF+15% $H_2O_2$ solution was used as a recovery solution for recovering impurities existing on the wafer surface, and this solution was run over the entire wafer surface, and collected.
(4) The Cu concentration in the recovery solution was determined by using AAS. As AAS, SIMAA-6000 produced by Perkin-Elmer was used.

As a result, the concentration of Cu recovered from the inside of the silicon wafer was determined to be about $1 \times 10^{11}$ atoms/cm$^2$ to $10 \times 10^{11}$ atoms/cm$^2$. That is, the recovery yield was about 0.3% at most. In addition, the values obtained in the evaluation fluctuated.

As described above, only about 0.1 to 0.3% of Cu was extracted from the silicon bulk in the annealing combined method, and thus it was found that the method had a problem as a quantitative evaluation. On the other hand, about 75% of Cu was recovered into concentrated sulfuric acid according to the present invention, although the recovery did not reach 100%. This is considered as a high recovery yield, and it can be seen that the evaluation for inside of the bulk could be attained.

EXAMPLE 2

Silicon wafers of which metal impurity contents were unknown were evaluated. Evaluation was performed for samples of wafers mirror-polished for one surface and having a diameter of 150 mm and thickness of 625 μm. The following wafers of different conductivity types and resistivities, which were obtained by different methods, were prepared and several wafers for each were evaluated: Sample 1: p-type 10 Ω·cm CZ wafer, Sample 2: p-type 0.015 Ω·cm CZ wafer, Sample 3: p-type 0.008 Ω·cm CZ wafer, Sample 4: n-type 10 Ω·cm CZ wafer, and Sample 5: p-type 10 Ω·cm FZ wafer.

The conditions of the pretreatment and analysis were the same as those used in Example 1.

As a result of the evaluation, the bulk Cu concentrations in the wafers were determined to be about $6 \times 10^{11}$ atoms/cm$^3$ to $8 \times 10^{11}$ atoms/cm$^3$ for Samples 1 and 5, and about $2 \times 10^{13}$ atoms/cm$^3$ to $3 \times 10^{13}$ atoms/cm$^3$ for Samples 2 and 3, and the concentration was below lower detection limit in Sample 4.

COMPARATIVE EXAMPLE 2

Wafers of the same specifications as those used in Example 2 were evaluated by the annealing combined method.

The condition of the evaluation was the same as those used in Comparative Example 1.

As a result of the evaluation, the bulk Cu concentrations in the wafers were below the lower detection limit or detected to be about $1 \times 10^{13}$ atoms/cm$^3$ or less for Samples 1, 4 and 5, and thus the Cu concentration was detected with fluctuation. In almost of wafers of Samples 2 and 3, the concentration was below the lower detection limit.

Thus, in the samples of low resistivity, the concentration was below the lower detection limit, and thus the measurement could not be performed. Further, also for the samples of ordinary resistivity, significant fluctuation was observed. When the cause of this fluctuation was investigated, it was found that contamination had been introduced during the annealing (heat treatment at 650° C.), which was a pretreatment before the analysis. In this evaluation method, care must be taken for, in particular, management of heat treatment furnace and so forth. On the other hand, according to the evaluation method of the present invention, although a heat treatment at about 200° C. was performed, it is a lower temperature compared with 650° C., and contamination is more unlikely to be introduced from the outside.

As described above, the evaluation can be performed for a wide range of resistivity according to the present invention, whereas the evaluation was scarcely possible for those of low resistivity according to the conventional method. Further, as for measurement precision and sensitivity, the present invention enabled evaluation of Cu for a low concentration of which measurement was difficult by the conventional methods.

What is claimed is:

1. A method for evaluating concentration of metal impurities contained in a silicon wafer, which comprises dropping concentrated sulfuric acid onto a surface of the silicon wafer, putting another uncontaminated wafer on the concentrated sulfuric acid on the silicon wafer to hold the concentrated sulfuric acid between the wafers, and subjecting the whole of the wafers in that state to a heat treatment to extract metal impurities solid-solubilized in the inside of the silicon wafer into the concentrated sulfuric acid, and chemically analyzing metal impurities contained in the concentrated sulfuric acid to evaluate concentration of metal impurities contained in the silicon wafer.

2. The method for evaluating concentration of metal impurities contained in a silicon wafer according to claim 1, wherein the heat treatment is performed at a temperature in the range of 100° C. to 290° C.

3. The method for evaluating concentration of metal impurities contained ill a silicon wafer according to claim 1, wherein the method of chemically analyzing metal impurities contained in the concentrated sulfuric acid comprises extracting metal impurities solid-solubilized in the inside of the silicon wafer into the concentrated sulfuric acid, then neutralizing the concentrated sulfuric acid on the silicon wafer by exposing it to an ammonia gas atmosphere, dropping a recovery solution for recovering metals remaining on the silicon wafer onto the wafer surface, running the recovery solution over the wafer surface, recovering the recovery solution and chemically analyzing the recovery solution.

4. The method for evaluating concentration of metal impurities contained in a silicon wafer according to claim 3, wherein the recovery solution consists of hydrofluoric acid/aqueous hydrogen peroxide, hydrochloric acid/aqueous hydrogen peroxide, hydrofluoric acid/nitric acid or aqua regia.

5. The method for evaluating concentration of metal impurities contained in a silicon wafer according to claim 3, wherein the chemical analysis is frameless atomic absorption spectrometry or inductively coupled plasma mass spectrometry.

6. The method for evaluating concentration of metal impurities contained in a silicon wafer according to claim 1, wherein the metal contained in the silicon wafer is Cu.

7. The method for evaluating concentration of metal impurities contained in a silicon wafer according to claim 2, wherein the metal contained in the silicon wafer is Cu.

8. The method for evaluating concentration of metal impurities contained in a silicon wafer according to claim 3, wherein the metal contained in the silicon wafer is Cu.

9. The method for evaluating concentration of metal impurities contained in a silicon wafer according to claim 4, wherein the metal contained in the silicon wafer is Cu.

10. The method for evaluating concentration of metal impurities contained in a silicon wafer according to claim 5, wherein the metal contained in the silicon wafer is Cu.

11. The method for evaluating concentration of metal impurities contained in a silicon wafer according to claim 1, wherein resistivity of the silicon wafer is 1 Ω·cm or less.

12. The method for evaluating concentration of metal impurities contained in a silicon wafer according to claim 2, wherein resistivity of the silicon wafer is 1 Ω·cm or less.

13. The method for evaluating concentration of metal impurities contained in a silicon wafer according to claimed wherein resistivity of the silicon wafer is 1 Ω·cm or less.

14. The method for evaluating concentration of metal impurities contained in a silicon wafer according to claim 4, wherein resistivity of the silicon wafer is 1 Ω·cm or less.

15. The method for evaluating concentration of metal impurities contained in a silicon wafer according to claim 5, wherein resistivity of the silicon wafer is 1 Ω·cm or less.

* * * * *